United States Patent
Kreitzer et al.

(12)

(10) Patent No.: US 6,196,228 B1
(45) Date of Patent: Mar. 6, 2001

(54) NASAL DILATOR

(75) Inventors: John T. Kreitzer; David F. Kreitzer, both of Scottsdale; Dan B. Pool, Phoenix, all of AZ (US)

(73) Assignee: CNS, Inc., Bloomington, MN (US)

( * ) Notice: Subject to any disclaimer, the term of this patent is extended or adjusted under 35 U.S.C. 154(b) by 75 days.

(21) Appl. No.: 08/756,060

(22) Filed: Nov. 26, 1996

(51) Int. Cl.$^7$ ...................................................... A61F 5/56
(52) U.S. Cl. ..................... 128/848; 602/902; 128/200.24; 606/204.45
(58) Field of Search ............................... 128/858, 200.24, 128/204.12, 207.18; 606/191, 196, 198, 199, 204.45; 602/901

(56) References Cited

U.S. PATENT DOCUMENTS

| | | |
|---|---|---|
| 1,292,083 | 1/1919 | Sawyer . |
| 5,476,091 * | 12/1995 | Johnson ................................ 606/199 |
| 5,479,944 | 1/1996 | Petruson . |
| 5,533,499 | 7/1996 | Johnson . |
| 5,533,503 | 7/1996 | Doubek et al. . |
| 5,553,605 * | 9/1996 | Muchin ................................ 128/848 |
| 5,611,333 * | 3/1997 | Johnson ................................ 128/848 |

* cited by examiner

*Primary Examiner*—Michael A. Brown
(74) *Attorney, Agent, or Firm*—Kinney & Lange, P.A.

(57) ABSTRACT

A nasal dilator for dilating a first nasal passage and a second nasal passage of a nose, including an elastic element having a first end and a second end, the elastic element movable toward an expanded configuration wherein the length of the elastic element increases, and biases to a retracted configuration wherein the length of the elastic element is reduced. The nasal dilator further includes an adhesive carried proximate the first end for attaching the first end to an outer wall of the first nasal passage, and an adhesive carried proximate the second end for attaching the second end to an outer wall of the second nasal passage.

14 Claims, 4 Drawing Sheets

NASAL DILATOR

BACKGROUND OF THE INVENTION

1. Field of the Invention

This invention relates to dilators.

More particularly, this invention relates to nasal dilators.

In a further and more specific aspect, the instant invention relates to a nasal dilator for maintaining one or more nasal passages of a nose in a dilated condition.

2. Prior Art

A portion of the human population has some malformation of the nasal passages which makes breathing difficult. Examples of such malformations are a deviated septum and swelling due to allergic reactions. The lower portion of the nostril immediately above the entrance to the nostril is known as a vestibule. The vestibule tapers inwardly to a narrowed neck-like area called the ostium internum. Above the ostium internum the nasal passages widen. Nasal obstructions commonly occur at the ostium in individuals who have swelling due to allergic reactions, a deviated septum or similar condition. Commonly, the lateral wall at the ostium is loose with the result that the outer wall tissue draws in during the process of inhalation to substantially block the passage of air through the nasal passage.

Blockages of the nasal passages is obviously very frustrating. In particular, sustained mouth breathing over a long period of time may cause lung irritation due to the inhalation of foreign particles that would otherwise be filtered if the breath had been passed through the nose. Blockage of the nasal passages i s particularly uncomfortable at night, since it is uncomfortable for many people who have such a problem to breathe through the mouth while asleep. Nasal blockage can lead to sleep disturbances and irregularities because those with such a condition may often wake during the night because of oxygen depletion.

The most common approach to a serious and chronic nasal blockage problem as described above is a surgical attempt to correct the malformation of the nasal passages. However, surgery is expensive and may not ultimately correct the problem.

As an alternative to surgery, nasal dilators for aiding breathing through the nose have been devised. One such nasal dilator includes generally elongated top and bottom rings which are spaced apart and connected together by a rear strut and a front strut. The front strut is longer than the rear strut and includes a bend therein formed at a position close to the front end of the bottom ring. When in place in the nasal passage, the top ring fits in the ostium within the nostril to prevent the tissue from being drawn in during inhalation, and to reduce extra flow resistance during exhalation. The bottom ring fits above the entrance to the nostril and serves to stabilize the position of the top ring within the nasal passage. One of these nasal dilators must be inserted into each nasal passage to provide unobstructed breathing.

However, these nasal dilators are not always effective because they are uncomfortable to wear and must be inserted within the nasal passages which can cause irritation and itching. In addition, these nasal dilators must be custom-made to fit each nasal passage of an individual.

Another known nasal dilator is comprised of a truss including a flexible strip of material having a first end region, a second end region and an intermediate segment. The first and second regions are adapted to engage the outer wall tissue of first and second nasal passages of the nose. The intermediate segment is configured to traverse a portion of the nose located between the first and second nasal passages. The truss member further includes first and second resilient bands secured to the strip of material adjacent opposite edges of the intermediate segment. The first and second resilient bands tend to return to their planar state. This motion acts to stabilize the outer wall tissue and thereby prevent the outer wall tissue of the first and second nasal passages from drawing in during breathing.

Although exemplary, this nasal dilator is difficult to construct, uncomfortable and unadjustable. It has been noticed that during use, the first end region and/or the second end region disengage the outer wall tissue of the respective nasal passages requiring a user to repeatedly engage either the first end region and/or the second end region with the outer wall tissue of the respective nasal passages for realizing the benefits of this nasal dilator. It is evident that there is a continuing need for improved nasal dilators.

It would be highly advantageous, therefore, to remedy the foregoing and other deficiencies inherent in the prior art.

Accordingly, it is an object of the present invention to provide a new and improved nasal dilator for preventing the outer wall tissue of nasal passages of a nose from drawing in during breathing.

Another object of the present invention is to provide a nasal dilator that is adjustable.

And another object of the present invention is to provide a nasal dilator that is easy to construct.

Still another object of the present invention is to provide a nasal dilator that is easy to install.

Yet another object of the instant invention is to provide a nasal dilator that is comfortable.

Yet still another object of the instant invention is to provide a nasal dilator that does not disengage during normal wear.

And a further object of the invention is to provide a nasal dilator that may be used for dilating a selected nasal passage.

SUMMARY OF THE INVENTION

Briefly, to achieve the desired objects of the instant invention in accordance with a preferred embodiment thereof, provided is a nasal dilator for dilating a first nasal passage and a second nasal passage of a nose. The nasal dilator includes an elastic element having a first end and a second end, the elastic element movable toward an expanded configuration wherein the length of the elastic element increases, and biases to a retracted configuration wherein the length of the elastic element is reduced. The nasal dilator further includes first engagement means carried proximate the first end for attaching the first end to an outer wall of the first nasal passage, and second engagement means carried proximate the second end for attaching the second end to an outer wall of the second nasal passage.

In a further aspect, the first engagement means and the second engagement means each include an adhesive for attaching the first end to the outer wall of the first nasal passage and attaching the second end to an outer wall of the second nasal passage.

In yet another aspect, the first engagement means and the second engagement means each include a first dilating element coupled to the first end, the first dilating element carrying an adhesive for attachment to the outer wall of the first nasal passage and a second dilating element coupled to the second end, the second dilating element carrying an adhesive for attachment to the outer wall of the second nasal passage.

Another embodiment of a nasal dilator for dilating a nasal passage, includes a rim having an inner surface engagable to the outer surface of the nasal passage, an outer surface, and defining a central opening. A cover is fixed to the outer surface of the rim and traverses the opening. Biasing means moves the cover between a normal distended orientation and a compressed orientation upon application of a compressive force, whereby the cover engages the outer wall of the nasal passage in the compressed orientation, and upon release of the compressive force the cover distends outwardly to the normal distended orientation, whereby the cover exerts a pull on the outer wall thereby maintaining the nasal passage in a dilated condition.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which.

DETAILED DESCRIPTION OF THE PREFERRED EMBODIMENT

Figure 1:
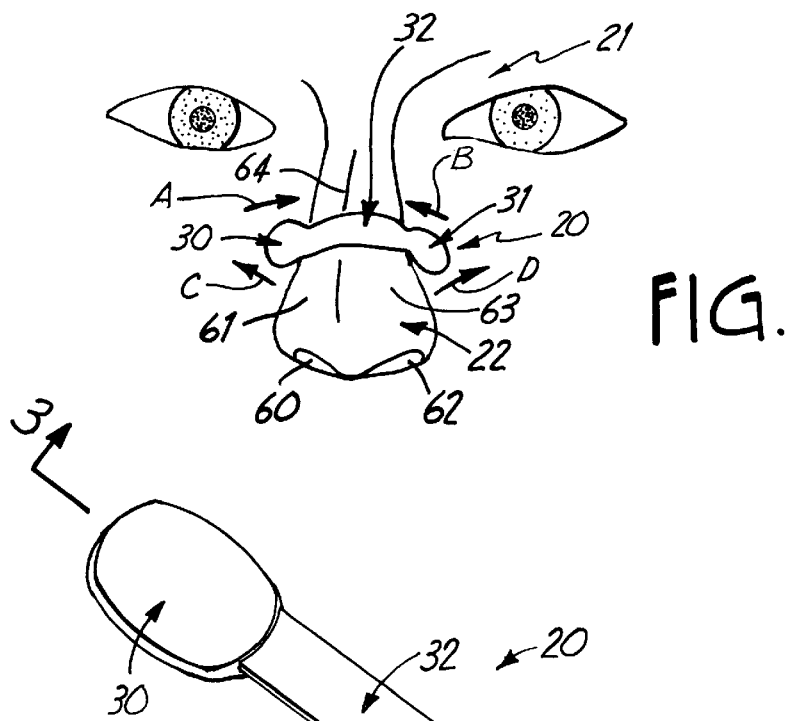
FIG. 1 is a perspective view of a nasal dilator shown as it would appear worn by a user, in accordance with a preferred embodiment of the present invention.

Turning now to the drawings, in which like reference characters indicate corresponding elements throughout the several views, attention is first directed to FIG. 1 illustrating a perspective view of a nasal dilator 20 shown as it would appear worn by a user 21, in accordance with a preferred embodiment of the present invention. In a further aspect, nasal dilator 20 is shown as it would appear secured to a nose 22 of user 21.

Figure 2:
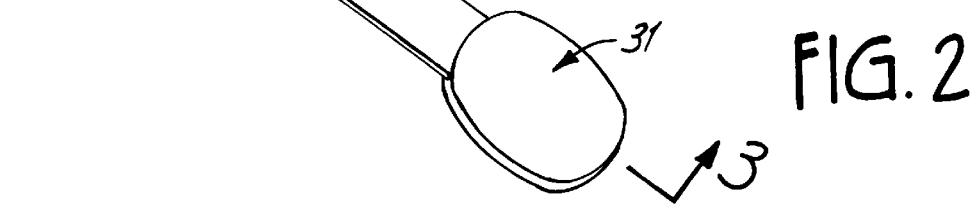
FIG. 2 is an enlarged upper perspective view of the nasal dilator of FIG. 1, in accordance with a preferred embodiment of the present invention.

With attention directed to FIG. 2, illustrated is an enlarged upper perspective view of nasal dilator 20 of FIG. 1. Nasal dilator 20 is generally comprised of a first dilating element 30, a second dilating element 31 and a bridge 32 interconnecting first dilating element 30 to second dilating element 31. As can be seen in FIG. 2, the width of bridge 32 is less than the width of first dilating element 30 and second dilating element 31, although this is not essential.

Figure 3:
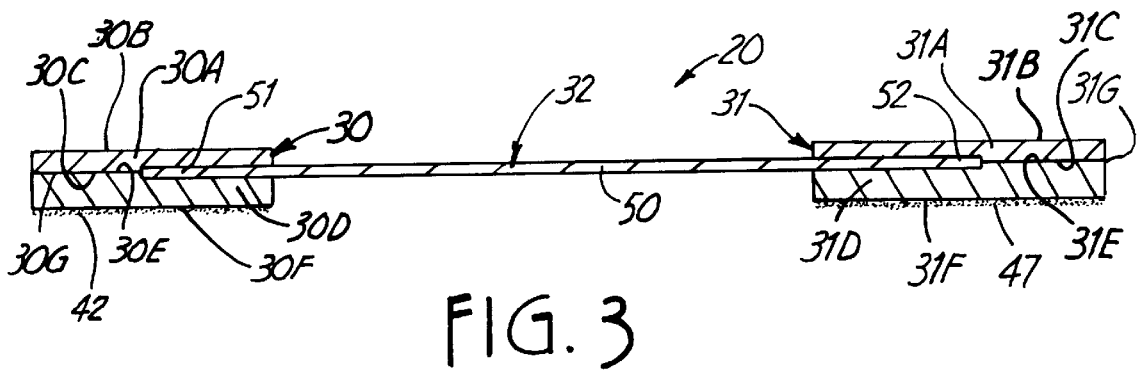
FIG. 3 is a sectional view taken along line 3—3 of FIG. 2, in accordance with a preferred embodiment of the present invention.

With continuing reference to FIG. 2 and additional reference to FIG. 3 illustrating a sectional view taken along line 3—3 of FIG. 2, first dilating element 30, preferably constructed of rubber, vinyl, cloth, soft plastic, or another selected material that is either substantially or somewhat pliant and resilient, has a substantially oval configuration and is generally comprised of a first layer 30A having an upper surface 30B and a lower surface 30C, a second layer 30D having an upper surface 30E and a lower surface 30F, an adhesive layer 30G adhesively coupling lower surface 30C of first layer 30A to upper surface 30E of second layer 30D, and an adhesive backing 42 carried by lower surface 30F. Adhesive backing 42 is shown as encompassing substantially all of lower surface 30C, although this is not essential. Bridge 32 interconnecting first dilating element 30 and second dilating element 31 is generally comprised of an elongate strip 50 preferably constructed of an elastic material having a first end 51 and a second end 52. Bridge 32 movable toward an expanded configuration wherein the length of elongate strip 50 increases, and biases to a retracted configuration wherein the length of elongate strip 50 is reduced. Due to the elasticity of elongate strip 50, bridge 32 will return to the retracted configuration from the expanded configuration. First end 51 of elongate strip 50 is sandwiched intermediate lower surface 30C of first layer 30A and upper surface 30E of second layer 30D and adhesively retained therebetween by means of adhesive layer 30G.

In like manner, second dilating element 31, preferably constructed of rubber, vinyl, cloth, soft plastic, or another selected material that is either substantially or somewhat pliant and resilient, has a substantially oval configuration and is generally comprised of a first layer 31A having an upper surface 31B and a lower surface 31C, a second layer 31D having an upper surface 31E and a lower surface 31F, an adhesive layer 31G adhesively coupling lower surface 31C of first layer 31A to upper surface 31E of second layer 31D, and an adhesive backing 47 carried by lower surface 31F. Adhesive backing 47 is shown as encompassing substantially all of lower surface 31F, although this is not essential. Second end 52 of elongate strip 50 is sandwiched intermediate lower surface 31C of first layer 31A and upper surface 31E of second layer 31D and adhesively retained therebetween by means of adhesive layer 31G.

With reference back to FIG. 1, nose 22 includes a first nasal passage 60 having an outer wall 61, a second nasal passage 62 having an outer wall 63 and a bridge 64 located between first nasal passage 60 and second nasal passage 62. To secure nasal dilator 20 to nose 22, first dilating element 30 is placed upon outer wall 61 of first nasal passage 60 so that adhesive backing 42, operative as an engagement means, engages outer wall 61 thereby adhesively and detachably engaging first dilating element 30 to outer wall 61 of first nasal passage 60. Bridge 32 is moved to the expanded configuration by pulling second dilating element 31 away from first dilating element 30 toward second nasal passage 62 with elongate strip 50 stretching therebetween as a result of the elastic nature of elongate strip 50. After pulling second dilating element 31 away from first dilating element 30 toward second nasal passage 62, second dilating element 31 is placed upon outer wall 63 of second nasal passage 62 so that adhesive backing 47, operative as an engagement means, engages outer wall 63 thereby adhesively and detachably engaging second dilating element 31 to outer wall 63 of second nasal passage 62. It will be understood that other methods of applying nasal dilator 20 can be used. For example, first dilator element 30 and second dilator element 31 can be grasped and pulled apart, stretching bridge 32 into the expanded configuration. Elements 31 and 32 are then placed on outer walls 61 and 63 respectively, with bridge 32 extending therebetween, over bridge 64 of nose 22.

After first dilating element 30 and second dilating element 31 are secured to first nasal passage 60 and second nasal passage 62, respectively, elongate strip 50 traverses bridge 64 of nose 22. Due to the elastic nature of elongate strip 50, elongate strip 50 operates as a biasing means for urging first dilating element 30 and second dilating element 31 upwardly and inwardly toward one another in the directions indicated by the arrowed lines A and B, respectively. As a result, outer wall 61 of first nasal passage 60 and outer wall 63 of second nasal passage 62 are pulled, distended or urged outwardly in the directions indicated by arrowed lines C and D, respectively, thereby placing first nasal passage 60 and second nasal passage 62 in a dilated condition thus increasing the volume of airflow passing therethrough as user 21 breathes.

Nasal dilator 20 effectively inhibits outer wall 61 of first nasal passage 60 and outer wall 63 of second nasal passage 62 from drawing in during breathing and maintains first nasal passage 60 and second nasal passage 62 in a dilated condition. Although other similarly operative biasing means may be used, elongate strip 50 constructed of an elastic material allows a user to adjust the degree or strength of the bias imparted by elongate strip 50 by altering the distance by which first dilating element 30 and second dilating element 31 are pulled apart during installation.

In particular, the farther apart first dilating element 30 and second dilating element 31 are pulled during installation, the degree of bias imparted by elongate strip 50 to pull first dilating element 30 and second dilating element 31 together increases thus increasing the degree of pull on outer wall 61 and outer wall 63 of first nasal passage 60 and second nasal passage 62, thereby increasing the degree of dilation of first nasal passage 60 and second nasal passage 62. Additionally, the degree of pull imparted to outer wall 61 and outer wall 63 of first nasal passage 60 and second nasal passage 62, respectively, decreases as the distance between first dilating element 30 and second dilating element 31 decreases during installation. Furthermore, due to the elastic nature of elongate strip 50, nasal dilator 20 is selectively adjustable for installation upon noses having varying sizes and shapes.

Figure 4:
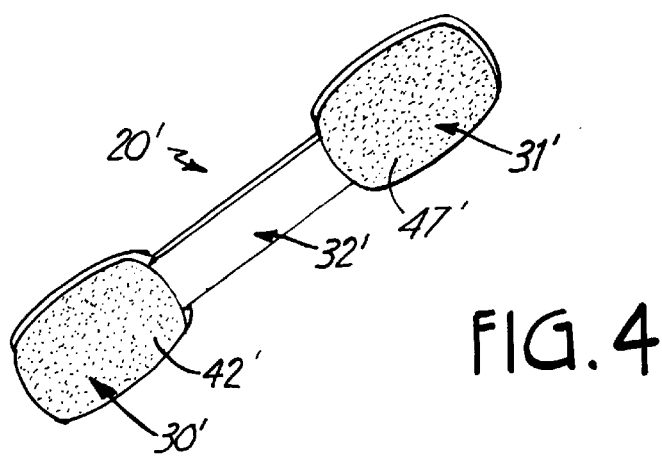
FIG. 4 is an enlarged lower perspective view of a further embodiment of a nasal dilator in accordance with a preferred embodiment of the present invention.

It will be readily understood by those having ordinary skill that although first dilating element 30 and second dilating element 31 have been disclosed as having a substantially oval shape, this is not essential and other shapes or configurations may be used. Additionally, with reference to FIG. 4, a nasal dilator 20' may be formed as a single unitary integral piece without departing from the nature and scope of the instant invention as herein disclosed. Specifically, dilator 20' can be formed entirely from an elastic element having opposing ends forming dilator members 30' and 31', and having an adhesive 42' thereon for attachment to the nose and coupled by a bridge 32'.

Figure 5:
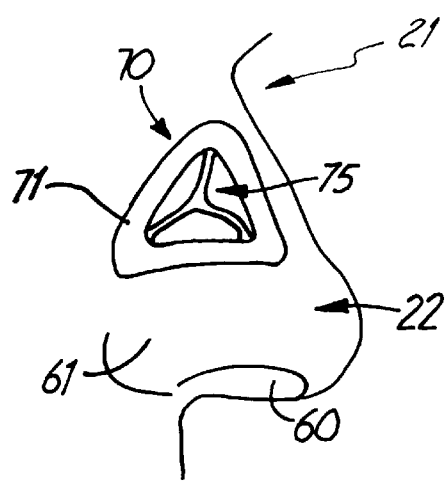
FIG. 5 is a perspective view of a dilating element comprised of a nasal dilator shown as it would appear worn by a user, in accordance with another embodiment of the present invention.

Attention is now directed to FIG. 5 illustrating a perspective view of a nasal dilator 70 shown as it would appear worn by user 21, in accordance with another embodiment of the present invention. For the purposes of discussion, nasal dilator 70 is shown as it would appear secured to outer wall 61 of first nasal passage 60, although this is not essential and nasal dilator 70 may be secured to outer wall 63 of second nasal passage 62 if desired.

Figure 6:
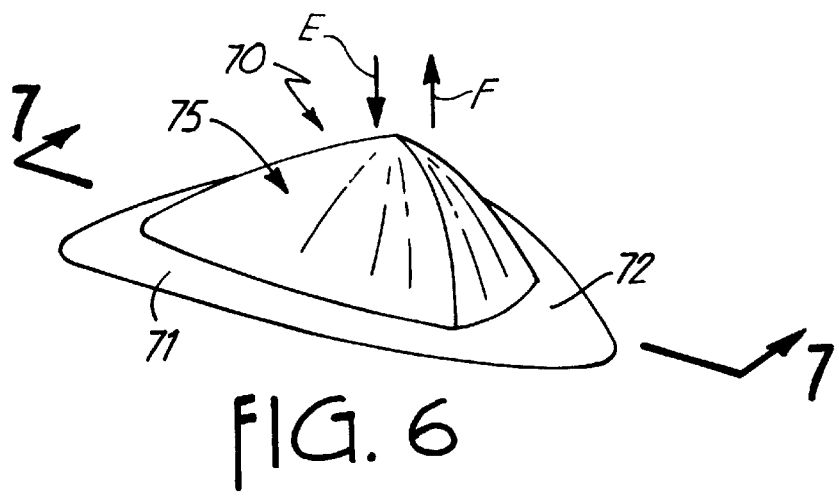
FIG. 6 is an enlarged perspective view of the nasal dilator of FIG. 5.
Figure 7:
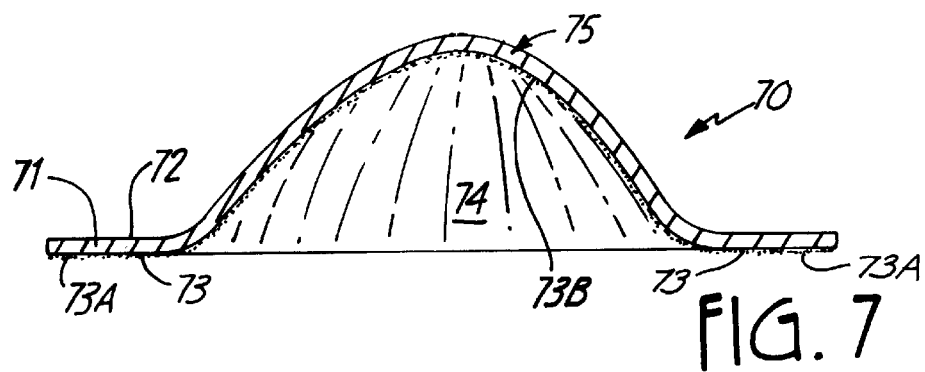
FIG. 7 is a sectional view taken along line 7—7 of FIG. 6.

With reference to FIG. 6 illustrating an enlarged perspective view of nasal dilator 70 of FIG. 5, and FIG. 7 illustrating a sectional view taken along line 7—7 of FIG. 6, nasal dilator 70 is generally comprised of a rim 71 bounding an opening 74 and having an upper surface 72, a lower surface 73 and an adhesive backing 73A carried by lower surface 73. Adhesive backing 73A is shown substantially encompassing the entire area of lower surface 73, although this is not essential. Rim 71 is formed generally in the shape of a triangle, although this is not essential and other shapes may be used. However, it will be readily understood that rim 71 of nasal dilator 70 is generally sized for placement upon the outer wall of a nasal passage of a selected user, such as outer wall 61 of first nasal passage 60, for reasons presently to appear.

Cover 75 is coupled to upper surface 72 of rim 71, traversing opening 74A, as a separate element or as an integrally formed element. Cover 75, has a shape which is deformable from a first shape into a second shape. In this embodiment, the first shape generally resembles a dome and is movable between a normal distended orientation as shown in FIG. 6, and a compressed orientation as shown in FIG. 5. To secure nasal dilator 70 to outer wall 61, rim 71 is placed upon outer wall 61 so that adhesive backing 73A, operative as an engagement means, engages outer wall 61 thereby being adhesively and detachably engaged to outer wall 61 with cover 75 present in the normal distended orientation. To dilate first nasal passage 60, compressive force is applied to cover 75, such as with a finger, in the direction indicated by the arrowed E for urging cover 75 inwardly for engaging adhesive backing 73B carried by cover 75 to outer wall 61. Upon release of the compressive force, cover 75 distends outwardly in the direction indicated by the arrowed line F to assume the normal distended orientation. As cover 75 distends outwardly in the direction indicated by the arrowed line F, outer wall 61 of first nasal passage 60 adhesively and detachably engaged to cover 75 is pulled or urged in the same direction thus placing first nasal passage 60 in a dilated condition thus increasing the volume of airflow passing therethrough as the user breaths.

It will be readily understood by those having ordinary skill that a pair of nasal dilators 70 may be interconnected with a bridge, such as bridge 32 discussed in combination with nasal dilator 20, if desired and consistent with the teachings of nasal dilator 20.

Figure 8:
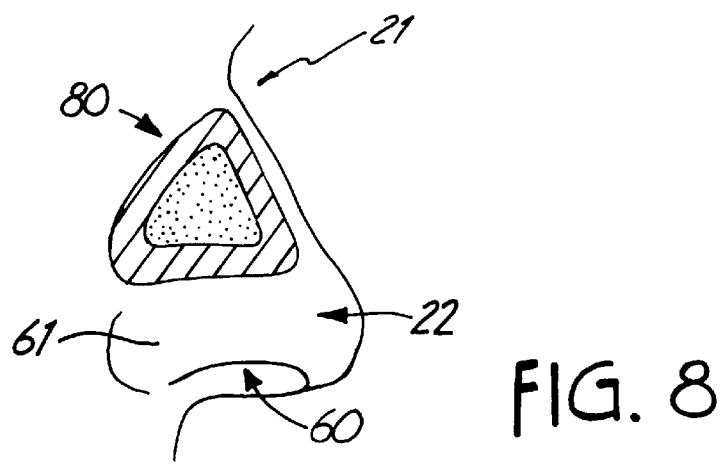
FIG. 8 is a perspective view of a dilating element comprised of a nasal dilator as it would appear worn by a user, in accordance with yet another embodiment of the present invention.

Reference is now directed to FIG. 8, illustrating a perspective view of a dilating element comprised of a nasal dilator 80 as it would appear worn by user 21, in accordance with yet another embodiment of the present invention. For the purposes of discussion, nasal dilator 80 is shown as it would appear secured to outer wall 61 of first nasal passage 60, although this is not essential and nasal dilator 80 may be secured to outer wall 63 of second nasal passage 62 if desired.

Figure 9:
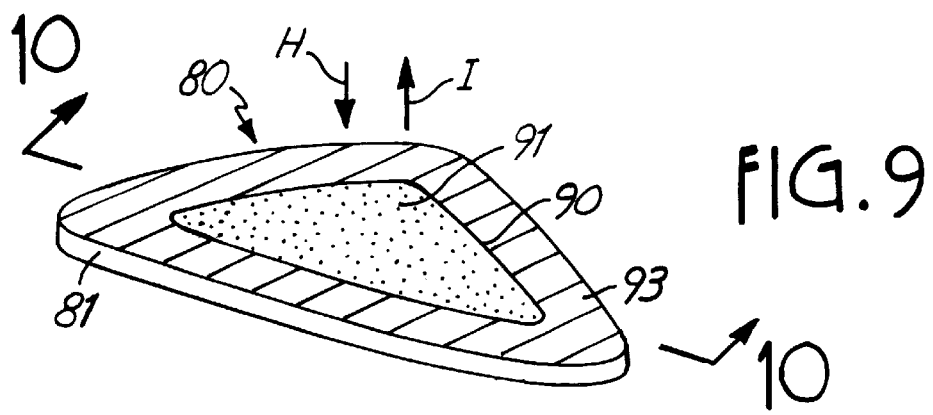
FIG. 9 is an enlarged perspective view of the nasal dilator of FIG. 8.
Figure 10:
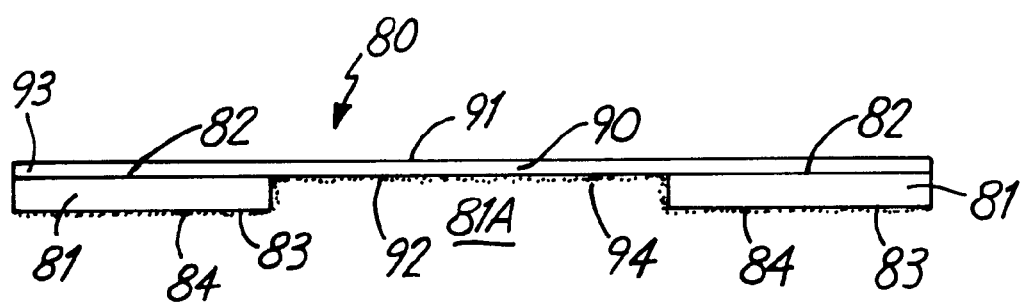
FIG. 10 is a sectional view taken along line 10—10 of FIG. 9.

With reference directed to FIG. 9 illustrating an enlarged perspective view of nasal dilator 80 of FIG. 8, and FIG. 10 illustrating a sectional view taken along line 10—10 of FIG. 9, nasal dilator 80 is generally comprised of a rim 81, preferably continuous, constructed of a selected compressible material, preferably foam, which will compress upon application of a compressive force and expand when the compressive force is removed. Continuous rim 81 defines an opening 81A and includes an upper surface 82, a lower surface 83 and an adhesive backing 84 carried by lower surface 83. Adhesive backing 83 is shown substantially encompassing the entire area of lower surface 82, although this is not essential. A cover 90 is also provided and carried by continuous rim 81, traversing opening 81A. Cover 90 includes an upper surface 91 and a lower surface 92 portions of which toward an outer perimeter edge 93 thereof being fixed to upper surface 82 of continuous rim 81 such that cover 90 traverses opening 81A. Preferably constructed of plastic, rubber, or the like, cover 90 may be fixed to upper surface 82 of continuous rim 81 by means of a conventional adhesive or other suitable coupling means. As shown in FIG. 9 and FIG. 10, portions of lower surface 92 of cover 90 traversing opening 81A carry an adhesive backing 94. Although not essential, adhesive backing 94 substantially encompasses the entire area of lower surface 92 of cover 90 traversing opening 81A.

To secure nasal dilator 80 to outer wall 61, continuous rim 81 is placed upon outer wall 61 so that adhesive backing 84, operative as an engagement means, carried by lower surface 83 engages outer wall 61 thereby adhesively and detachably engaging continuous rim 81 to outer wall 61. To dilate first nasal passage 60, compressive force may be applied to cover 90 and continuous rim 81, such as with the fingers of a hand, in the direction indicated by the arrowed H for compressing continuous rim 81 constructed of the foam material and for urging lower surface 92 of cover 90 inwardly for engaging adhesive backing 94 carried by lower surface 92 of cover 90 to outer wall 61. Upon release of the compressive force, the foam material of continuous rim 81 operates as a biasing means for expanding or decompressing and thereby distending outwardly in the direction indicated by the arrowed line I. As continuous rim 81 distends outwardly in the direction indicated by the arrowed line I as continuous rim 81 distends, lower surface 92 of cover 90 adhesively and detachably engaged to outer wall 61 of first nasal passage 60 is carried outwardly by continuous rim 81 in the same direction thereby pulling outer wall 61 outwardly placing first nasal passage 60 in a dilated condition thus increasing the volume of airflow passing therethrough as the user breaths.

It will be readily understood by those having ordinary skill that a pair nasal dilators 80 may be interconnected with a bridge, such as bridge 32 discussed in combination with nasal dilator 20, if desired and consistent with the teachings of nasal dilator 20.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A nasal dilator for dilating a first nasal passage and a second nasal passage of a nose, comprising:
    a first dilating element engagable to the outer wall of a first nasal passage;
    a second dilating element engagable to the outer wall of a second nasal passage;
    a bridge element traversing the nose and interconnecting the first dilating member and the second dilating member, the bridge includes an elastic element movable toward an expanded configuration wherein the length of the elastic element increases, and biases to a retracted configuration wherein the length of the elastic element is reduced.

2. The nasal dilator of claim 1, wherein the first dilating element includes engagement means for detachably engaging the first dilating element to an outer wall of the first nasal passage.

3. The nasal dilator of claim 1, wherein the second dilating element includes engagement means for detachably engaging the second dilating element to an outer wall of the second nasal passage.

4. The nasal dilator of claim 3, wherein said engagement means includes an adhesive backing.

5. The nasal dilator of claim 4, wherein said engagement means includes an adhesive backing.

6. A nasal dilator for dilating a first nasal passage and a second nasal passage of a nose, comprising:
    an elastic element having a first end and a second end, the elastic element movable toward an expanded configuration wherein the length of the elastic element increases, and biases to a retracted configuration wherein the length of the elastic element is reduced;
    first engagement means carried proximate the first end for attaching the first end to an outer wall of the first nasal passage; and
    second engagement means carried proximate the second end for attaching the second end to an outer wall of the second nasal passage.

7. A nasal dilator as claimed in claim 6 wherein the first engagement means and the second engagement means each include an adhesive for attaching the first end to the outer wall of the first nasal passage and attaching the second end to an outer wall of the second nasal passage.

8. A nasal dilator as claimed in claim 6 wherein the first engagement means and the second engagement means each include:
    a first dilating element coupled to the first end, the first dilating element carrying an adhesive for attachment to the outer wall of the first nasal passage;
    a second dilating element coupled to the second end, the second dilating element carrying an adhesive for attachment to the outer wall of the second nasal passage.

9. A nasal dilator as claimed in claim 8 wherein the first dilating element and the second dilating element are each formed of a pliant material.

10. The nasal dilator of claim 6 wherein engagement means includes an adhesive for attaching first and second ends to outer walls of the first and second nasal passages.

11. The nasal dilator of claim 10 wherein said engagement means is adhered to said elastic element.

12. A nasal dilator for dilating a first nasal passage and a second nasal passage of a user's nose, the dilator comprising:
    an elastic element having a first end and a second end, the elastic element stretchable toward an expanded configuration wherein the length of the elastic element is increased, and in which configuration the first end and the second end tend to be pulled toward one another so as to tend to reduce the increased length; and
    an engagement means on the elastic element for attaching the first end and the second end thereof to outer walls of the first and second nasal passages.

13. The nasal dilator of claim 12 wherein said engagement means is adhered to said elastic element.

14. The dilator of claim 10 wherein said elastic element is reduced in length from said increased length in being adhered by said engagement means to outer wall tissues of said first and second nasal passages.

* * * * *